US011813328B2

(12) United States Patent
Sloey et al.

(10) Patent No.: US 11,813,328 B2
(45) Date of Patent: Nov. 14, 2023

(54) METHODS FOR REDUCING THE VISCOSITY OF LIQUID PHARMACEUTICAL FORMULATIONS COMPRISING THERAPEUTIC PROTEINS

(71) Applicant: AMGEN INC., Thousand Oaks, CA (US)

(72) Inventors: Christopher James Sloey, Newbury Park, CA (US); Sekhar Kanapuram, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/521,057

(22) PCT Filed: Oct. 22, 2015

(86) PCT No.: PCT/US2015/056972
§ 371 (c)(1),
(2) Date: Apr. 21, 2017

(87) PCT Pub. No.: WO2016/065181
PCT Pub. Date: Apr. 28, 2016

(65) Prior Publication Data
US 2017/0333559 A1    Nov. 23, 2017

Related U.S. Application Data

(60) Provisional application No. 62/067,637, filed on Oct. 23, 2014.

(51) Int. Cl.
*A61K 39/395* (2006.01)
*A61K 47/18* (2017.01)
*A61K 9/19* (2006.01)
A61K 9/00 (2006.01)

(52) U.S. Cl.
CPC .......... *A61K 39/39591* (2013.01); *A61K 9/19* (2013.01); *A61K 39/3955* (2013.01); *A61K 47/183* (2013.01); A61K 9/0019 (2013.01); C07K 2317/90 (2013.01)

(58) Field of Classification Search
CPC .......... A61K 39/3955; A61K 39/39591; A61K 9/19; A61K 47/183; A61K 9/0019; C07K 2317/90
See application file for complete search history.

(56) References Cited

U.S. PATENT DOCUMENTS

| 6,767,892 B1 | 7/2004 | Shirley et al. |
| 7,153,507 B2 | 12/2006 | van de Winkel et al. |
| 7,592,429 B2 | 9/2009 | Paszty et al. |
| 7,648,702 B2 | 1/2010 | Gombotz et al. |
| 7,906,625 B2 | 3/2011 | Shen et al. |
| 7,982,016 B2 | 7/2011 | Comeau et al. |
| 8,030,467 B2 | 10/2011 | Seth et al. |
| 8,062,640 B2 | 11/2011 | Sleeman et al. |
| 8,080,243 B2 | 12/2011 | Liang et al. |
| 8,101,182 B2 | 1/2012 | Dong et al. |
| 8,232,372 B2 | 7/2012 | Presta et al. |
| 8,545,849 B2 | 10/2013 | Borras et al. |
| 8,715,663 B2 | 5/2014 | Paszty et al. |
| 8,961,964 B2 | 2/2015 | Liu et al. |
| 11,464,857 B2 | 10/2022 | Sloey et al. |
| 2004/0197324 A1* | 10/2004 | Liu ................ A61K 9/0019 424/130.1 |
| 2005/0037084 A1 | 2/2005 | Nomura et al. |
| 2005/0176109 A1 | 8/2005 | Yumioka et al. |
| 2009/0186022 A1 | 7/2009 | Bardroff et al. |
| 2009/0291076 A1 | 11/2009 | Morichika et al. |
| 2012/0270782 A1* | 10/2012 | Gopinath ........... A61K 9/0019 514/8.6 |
| 2013/0171128 A1 | 7/2013 | Huang et al. |
| 2014/0206845 A1 | 7/2014 | Kameoka et al. |
| 2014/0370003 A1 | 12/2014 | Winter |
| 2015/0004174 A1 | 1/2015 | Wasserman et al. |
| 2017/0333559 A1 | 11/2017 | Sloey et al. |
| 2018/0237501 A1 | 8/2018 | Sloey et al. |

FOREIGN PATENT DOCUMENTS

| EP | 0 804 163 B1 | 11/2003 |  |
| EP | 1 977 763 A1 | 10/2008 |  |
| EP | 2080504 A2 * | 7/2009 | ............ A61P 29/00 |
| JP | 2011-067202 A1 | 4/2011 |  |
| WO | 1990000397 A1 | 1/1990 |  |
| WO | WO 1999/024063 A1 | 5/1999 |  |
| WO | WO 2000/24782 A2 | 5/2000 |  |
| WO | WO 2002/038170 A2 | 5/2002 |  |
| WO | WO 2004/055164 A2 | 7/2004 |  |
| WO | WO 2004/066957 A2 | 8/2004 |  |
| WO | 2007074880 A1 | 7/2007 |  |

(Continued)

OTHER PUBLICATIONS

Inoue et al. 2014. Mol. Pharm. 11:1889-1896 (Year: 2014).*
Arakawa et al., Suppression of Protein Interactions by Arginine: A Proposed Mechanism of the Arginine Effects, *Biophys. Chem.* (2007) 127(1):1-8.
Baynes et al., Rational Design of Solution Additives for the Prevention of Protein Aggregation, *Biophysical Journal* (2004), 87:1631-1639.
Baynes et al., Role of Arginine in the Stabilization of Proteins Against Aggregation, *Biochemistry* (2005), 44:4919-4925.
Chaudhri et al., The Role of Amino Acid Sequence in the Self-Association of Therapeutic Monoclonal Antibodies: Insights from Coarse-Grained Modeling, *J. Phys. Chem. B* (2013), 117(5):1269-1279.

(Continued)

*Primary Examiner* — Robert S Landsman
(74) *Attorney, Agent, or Firm* — Julie J. Hong (57) ABSTRACT

A method for reducing the viscosity of a pharmaceutical formulation is provided that utilizes a viscosity-reducing concentration of an excipient selected from the group consisting of the n-acetyl arginine, n-acetyl lysine, n-acetyl proline and mixtures thereof in combination with a therapeutiv protein. A stable pharmaceutical formulation is also provided.

35 Claims, 2 Drawing Sheets

(56) References Cited

FOREIGN PATENT DOCUMENTS

| WO | 2009026558 A1 | 2/2009 |
| WO | 2009/073569 A2 | 6/2009 |
| WO | 2011/095543 A1 | 8/2011 |
| WO | WO 2011/104381 A2 | 9/2011 |
| WO | WO 2011/139718 A1 | 11/2011 |
| WO | 2013166448 A1 | 11/2013 |
| WO | 2013186230 A1 | 12/2013 |
| WO | 2015/173782 A1 | 11/2015 |
| WO | 2012154999 A1 | 11/2015 |
| WO | 2016065181 A1 | 4/2016 |
| WO | 2016/087569 A1 | 6/2016 |
| WO | 2018064307 A2 | 4/2018 |
| WO | 2018067987 A1 | 4/2018 |

OTHER PUBLICATIONS

Cheng et al., Linking the Solution Viscosity of an IgG2 Monoclonal Antibody to its Structure as a Function of pH and Temperature, *J. Pharm Sci.* (2013), 102:4291-4304.

Chennamsetty et al., Design of Therapeutic Proteins with Enhanced Stability, *Proceedings of the National Academy of Sciences of the United States of America* (2009), 106:11937-11942.

Connolly et al., Weak Interactions Govern the Viscosity of Concentrated Antibody Solutions: High-Throughput Analysis Using the Diffusion Interaction Parameter, *Biophys. J.* (2012), 103:69-78.

Das et al., Inhibition of Protein Aggregation: Supramolecular Assemblies of Arginine Hold the Key, *A. PLoS ONE* (2007), w:e1176.

Guo et al., Structure-Activity Relationship for Hydrophobic Salts as Viscosity-Lowering Excipients for Concentrated Solutions of Monoclonal Antibodies, *Pharm Res* (2012), 29(11):3102-3109.

Hamada et al., Effect of Additives on Protein Aggregation, *Curr. Pharm. Biotechnol.* (2009) 10(4):400-407.

Inoue et al., Arginine and Lysine Reduce the High Viscosity of Serum Albumin Solutions for Pharmaceutical Injection, *Journal of Bioscience and Bioengineering.* (2014) 117(5):539-543.

Inoue et al., Specific Decrease in Solution Viscosity of Antibodies by Arginine for Therapeutic Formulations, *Molecular pharmaceutics* (2014), 11:1889-1896.

Ishibashi et al., Is Arginine a Protein-Denaturant?, *Protein Expr. Purif.* (2005) 42(1):1-6.

Jouyban et al., Review of Pharmaceutical Applications of N-Methyl-2-Pyrrolidone, *J. Pharm. Pharmaceut. Sci.* (2010), 13(4):524-535.

Kamerzell et al., Polar Solvents Decrease the Viscosity of High Concentration IgG1 Solutions through Hydrophobic Solvation and Interaction: Formulation and Biocompatibility Considerations, *J. Pharm Sci* (2013), 102(4):1182-1193.

Ketchem et al., Mitigation of monoclonal antibody viscosity by modification of protein surface charge, *Ninth Annual PEGS Summit*, Apr. 29-May 3, 2013, Boston, MA (2013).

Li et al., Concentration Dependent Viscosity of Monoclonal Antibody Solutions: Explaining Experimental Behavior in Terms of Molecular Properties, *Pharm. Res.* 31 (2014), 3161-3178.

Lutz et al., High Concentration Biotherapeutic Formulation and Ultrafiltration: Part 1 Pressure Limits, *Biotechnol. Prog.* (2016), 00(00):1-12.

Neergaard et al., Viscosity of High Concentration Protein Formulations of Monoclonal Antibodies of The IgGl And IgG4 Subclass—Prediction Of Viscosity Through Protein-Protein Interaction Measurements, *Eur. J. Pharm Sci.* (2013), 49(3):400-410.

Nichols et al., Rational Design of Viscosity Reducing Mutants of a Monoclonal Antibody: Hydrophobic Versus Electrostatic Inter-Molecular Interactions, *mAbs* (2015), 7(1):212-230.

Schneider et al., Arginine and the Hofmeister Series: The Role of Ion-Ion Interactions in Protein Aggregation Suppression, *J. Phys. Chem B.* (2011), 115(2):7447-7458.

Schneider et al., Effects of Solute-Solute Interactions on Protein Stability Studied Using Various Counterions and Dendrimers, *PloS ONE* (2011), 6:e27665.

Sharma et al., In silico Selection of Therapeutic Antibodies for Development: Viscosity, Clearance, and Chemical Stability, *Proc. Natl. Acad. Sci. U. S. A 111* (2014), 18601-18606.

Shukla et al., Complex Interactions between Molecular Ions in Solution and Their Effect on Protein Stability, *J. Am. Chem. Soc.* (2011), 133:18713-18718.

Shulka et al., Interaction of Arginine with Proteins and the Mechanism by which it Inhibits Aggregation, *The Journal of Physical Chemistry. B* (2010),114:13426-13438.

Shulka et al., Molecular Level Insight into Intra-Solvent Interaction Effects on Protein Stability and Aggregation, *Advanced Drug Delivery Reviews* (2011), 63:1074-1085.

Singh et al., Dipole-Dipole Interaction in Antibody Solutions: Correlation with Viscosity Behavior at High Concentration, *Pharm Res* (2014), 31(9):2549-2558.

Tsumoto et al., Review: Why is Arginine Effective in Suppressing Aggregation?, *Protein & Peptide Letters* (2005) 12:613-619.

Tsumoto et al., Role of Arginine in Protein Refolding, Solubilization, and Purification, *Biotechnol. Prog.* (2004), 20:1301-08.

Voynov et al., Predictive Tools for Stabilization of Therapeutic Proteins. *mAbs* (2009), 1:580-582.

Yadav et al., Specific Interactions in High Concentration Antibody Solutions Resulting in High Viscosity, *J. Pharm. Sci.* (2010) 99(3):1152-1168.

Yadav et al., The Influence of Charge Distribution on Self-Association and Viscosity Behavior of Monoclonal Antibody Solutions, *Mol. Pharm* (2012), 9(4):791-802.

Yadav et al., Viscosity Behavior of High-Concentration Monoclonal Antibody Solutions: Correlation with Interaction Parameter and Electroviscous Effects, *J. Pharm Sci.* (2012), 101(3):998-1011.

Office Action dated Mar. 31, 2020 in Chinese Application No. 201580057461.5 (with English Translation).

Arakawa et al., "Recombinant Production of Native Proteins from *Escherichia coli*", Rational Design of Stable Protein Formulations, Theory and Practice, edited by Carpenter and Manning, Springer (2002), 27-60.

Binabaji et al., Intermolecular Interactions and the Viscosity of Highly Concentrated Monoclonal Antibody Solutions, Pharm. Res. (2015) 32:3102-3109.

Binabaji et al., Theoretical Analysis of the Ultrafiltration Behavior of Highly Concentrated Protein Solutions, Journal oi Membrane Science 494 (2015) 216-223.

Binabaji et al., Ultrafiltration of Highly Concentrated Antibody Solutions: Experiments and Modeling for the Effects of Module and Buffer Conditions, Biotechnol. Prog. (2016), 32(3): 692-701.

Carpenter and Manning, Rational Design of Stable Protein Formulations, Theory and Practice, Pharm. Biotech. (2002), 13:1-222.

Cunningham et al., Structural and biophysical studies of PCSK9 and its mutants linked to familial hypercholesterolemia, Nat Struct Mol Biol (2007), 14(5), 413-419.

Examination report No. 1 dated Dec. 11, 2019 in AU Application No. 2015335743.

Examination report No. 2 dated Dec. 3, 2020 in AU Application No. 2015335743.

Ferrara et al., "Recombinant renewable polyclonal antibodies", 2015, mAbs, vol. 7, Issue 1: pp. 32-42, Taylor & Francis Group, LLC.

First Office Action dated Jan. 8, 2021 in Mexican Application No. MX/a/2017/005243 (with English translation).

First Official Action dated Apr. 23, 2019 in Japanese Patent Application No. 2017-522169 (with English translation).

First Official Action dated Nov. 4, 2020 in Japanese Patent Application No. 2019-191701 (with English translation).

Horton et al., "Molecular biology of PCSK9: its role LDL metabolism", Trends Biochem Sci., vol. 32 (2), pp. 71-77 (2007).

International Search Report dated Dec. 16, 2015 in PCT Application No. PCT/US2015/056972.

Jezek et al., « Viscosity of concentrated therapeutic protein compositions », Advanced Drug Delivery Reviews 63 (2011) pp. 1107-1117.

Joshi et al. Aggregation of Monoclonal Antibody Products: Formation and Removal, BioPharm International, Mar. 1, 2013, 7 pages. vol. 26(, Issue 3.

(56) References Cited

OTHER PUBLICATIONS

Office Action dated Apr. 15, 2021 in Chinese Application No. 201580057461.5 (with English translation).
Office Action dated Feb. 19, 2021in CL Application No. 201902190 (with English translation).
Office Action dated May 6, 2020 in Israel Application No. 251726 (with English translation).
Office Action dated Nov. 18, 2019 in Indian Application No. 201717014850.
Office Action dated Nov. 29, 2021 in Canadian Application No. 2,964,786.
Office Communication dated Jan. 3, 2020 in EP Application No. 15 790 759.3.
Official Action dated Dec. 18, 2017 in Eurasia Application No. 201790787 (with English translation).
Piper et al., "The crystal structure of PCSK9: a regulator of plasma LDL-cholesterol", Structure, vol. 15 (5), pp. 545-552 (2007).
Rishi et al., Role of Non-Compatible Osmolytes in the Stabilization of Proteins During Heat Stress, Biochem. J. (1998), 329:137-143.
Rudikoff et al., "Single Amino Acid Substitution Altering Antigen-Binding Specificity", Proc. Natl. Acad. Sci. U S A., vol. 79, pp. 1979-1983 (1982).
Second Office Action dated Jun. 15, 2021 in Mexican Application No. MX/a/2017/005243 (with English translation).
Seidah et al., "The Secretory Proprotein Convertase Neural Apoptosis-Regulated Convertase 1 (NARC-1): Liver Regeneration and Neuronal Differentiation", PNAS, vol. 100 (3), pp. 928-933 (Feb. 4, 2003).
Seidah et al., The proprotein convertases are potential2011 targets in the treatment of dyslipidemia, J Mol Med (Berl) (2007), 85(7), 685-696.
Wang et al., "Viscosity-Lowering Effect of Amino Acids and Salts on Highly Concentrated Solutions of Two IgG1 Monoclonal Antibodies," Mol. Pharmaceutics, vol. 12 (12), pp. 4478-4487 (2015).
Written Opinion dated Dec. 16, 2015 in PCT Application No. PCT/US2015/056972.
Written Opinion dated Jul. 14, 2020 in SG Application No. 11201703152R.
Office Action dated Oct. 22, 2020 in Chilean Application No. 201902362.
Office Action dated Mar. 22, 2021 in EA Application No. 201991951.
Communication dated Nov. 12, 2019 in EP Application No. 18710193.6.
First Office Action dated Dec. 21, 2021 in JP Application No. 2018-023742.
Written Opinion dated Jan. 29, 2021 in SG Application No. 11201907505T.
International Search Report dated May 9, 2018 in PCT/US2018/019189.
Written Opinion dated May 9, 2018 in PCT/US2018/019189.
Office Action dated Dec. 26, 2019 in U.S. Appl. No. 15/902,775.
Office Action dated Jul. 31, 2020 in U.S. Appl. No. 15/902,775.
Office Action dated Dec. 20, 2021 in U.S. Appl. No. 15/902,775.
Srivastava et al., "Viscosity Reduction and Stability Enhancement of Monoclonal Antibody Formulations Using Derivatives of Amino Acids", Journal of Pharmaceutical Sciences, (2022) pp. 1-9, in press, corrected proof DOI: 10.1016/j.xphs.2022.05.011.
Notice of Allowance and Fees Due dated May 18, 2022 in U.S. Appl. No. 15/902,775.
Notice of Preliminary Rejection dated Jul. 26, 2022 for Korean Patent Application 10-2017-7011706 with English translation.
Office Action dated Jun. 1, 2022 in Chilean patent application 201700984 with English translation.
Office Action in Brazilian Patent Application No. 1120170081253 dated Oct. 25, 2022 with machine translation.
Office Action in Japanese Patent Application No. 2018-023742 dated Jun. 6, 2023 with English translation.
Office Action in Japanese Patent Application No. 2021-170676 dated Jun. 6, 2023 with English translation.
Office Action in Chinese Patent Application No. 201880025966.7 dated Aug. 16, 2023 with English translation.
Office Action in Chinese Patent Application No. 202210048275.7 dated Jul. 29, 2023 with English translation.
Binabaji, Elaheh, Ultrafiltration of Highly Concentrated Monoclonal Antibody Solutions, The Pennsylvania State University, The Graduate School, College of Engineering, Thesis (2015) 1-190.
Office Action and Search Report in Chilean Patent Application No. 201902362 dated Oct. 29, 2021 with summary English translation.
Office Action in Japanese Patent Application No. 2018-023742 dated Oct. 4, 2022 with English translation.
Office Action in Eurasian Patent Application No. 201991951 dated Dec. 21, 2022 with English translation.
Office Action in Canadian Patent Application No. 3,053,394 dated Aug. 2, 2023.
Office Action in Korean Patent Application No. 10-2019-7026969 dated Aug. 28, 2023 with English translation.
Communication in EP Patent Application No. 18710193.6 dated Apr. 3, 2023.
Office Action in Brazilian Patent Application No. 1120170081253 dated May 16, 2023 with machine translation.
Office Action in Israeli Patent Application No. 287947 dated Feb. 16, 2023.
Office Action in Mexican Patent Application No. MX/a/2019/009952 dated May 24, 2023 with English translation.
Office Action in Japanese Patent Application No. 2021-170676 dated Dec. 13, 2022 with English translation.
Office Action in Brazilian Patent Application No. 1120170081253 dated Feb. 7, 2023 with machine translation.
Office Action in Korean Patent Application No. 10-2019-7026969 dated Feb. 9, 2023 with English translation.

* cited by examiner

METHODS FOR REDUCING THE VISCOSITY OF LIQUID PHARMACEUTICAL FORMULATIONS COMPRISING THERAPEUTIC PROTEINS

CROSS-REFERENCE TO RELATED APPLICATIONS

This application is a National Stage application under 35 U.S.C. § 371 of International Application No, PCT/US15/56972, having an international filing date of Oct. 22, 2015, which claims the benefit of U.S. Provisional Patent Application No. 62/067,637, filed Oct. 23, 2014, all of which are incorporated herein by reference in their entirety for all purposes.

BACKGROUND

Pharmaceutically active proteins, such as antibodies, are frequently formulated in liquid solutions, particularly for parenteral injection. For products that need to be administered via a subcutaneous route, for example use in self administration; formulations in delivery volumes greater than 1-2 milliliters are not well tolerated. In such cases highly concentrated protein formulations are desirable to meet the limited dose volume. The high dose and small volume requirements such administration means that the protein therapeutic can reach concentrations of upwards of 100 mg/ml or more. Highly concentrated protein formulations can pose many challenges to the manufacturability and administration of protein therapeutics. One challenge posed by some highly concentrated protein formulations is increased viscosity. High viscosity formulations are difficult to handle during manufacturing, including at the bulk and filling stages. High viscosity formulations are also difficult to draw into a syringe and inject, making administration to the patient difficult and unpleasant. The need to identify compounds that are useful for reducing viscosity of highly concentrated protein formulations, to develop methods of reducing the viscosity of such formulations, and to provide pharmaceutical formulations with reduced viscosity are well known in the pharmaceutical industry. The present invention provides such compounds, methods and formulations.

SUMMARY

Provided is an excipient selected from the group consisting of n-acetyl arginine, n-acetyl lysine, n-acetyl histidine, n-acetyl proline and mixtures thereof at selected concentrations for use in reducing the viscosity of protein formulations. Methods for reducing the viscosity of protein formulations by combining a high concentration therapeutic protein with a viscosity-reducing concentration of an excipient selected from the group consisting of n-acetyl arginine, n-acetyl lysine, n-acetyl histidine, n-acetyl proline and mixtures thereof are provided herein. Also provided is lyophilized powder comprising a therapeutic protein and an excipient selected from the group consisting of n-acetyl arginine, n-acetyl lysine, n-acetyl histidine, n-acetyl proline and mixtures thereof wherein the excipient is present at a weight:weight concentration effective to reduce viscosity upon reconstitution with a diluent. Also provided is a lyophilized powder comprising a therapeutic protein and a diluent for reconstitution that contains an excipient selected from the group consisting of n-acetyl arginine, n-acetyl lysine, n-acetyl histidine, n-acetyl proline and mixtures thereof.

Provided herein is a method for reducing the viscosity of a liquid pharmaceutical formulation comprising a therapeutic protein at a concentration of at least 70 mg/ml, comprising the step of combining the therapeutic protein with a viscosity-reducing concentration of an excipient selected from the group consisting of n-acetyl arginine, n-acetyl lysine, n-acetyl histidine, n-acetyl proline and mixtures thereof. In one embodiment the viscosity of the formulation is reduced by at least 5%. In another embodiment the viscosity of the formulation is reduced by at least 10%. In another embodiment the viscosity of the formulation is reduced by at least 20%. In another embodiment the viscosity of the formulation is reduced by at least 30%. In another embodiment the viscosity of the formulation is reduced by at least 40%. In another embodiment the viscosity of the formulation is reduced by at least 50%. In another embodiment the viscosity of the formulation is reduced by at least 60%. In another embodiment the viscosity of the formulation is reduced by at least 70%. In another embodiment the viscosity of the formulation is reduced by at least 80%. In a related embodiment, pharmaceutical formulations produced by such methods are provided.

Also provided is a pharmaceutical composition comprising a therapeutic protein at a concentration of at least 70 mg/mL, and an excipient selected from the group consisting of n-acetyl arginine, n-acetyl lysine, n-acetyl histidine, n-acetyl proline and mixtures thereof. In one embodiment the concentration of the excipient is from about 5 mM to about 700 mM. In a related embodiment the concentration of the excipient is from about 100 mM to about 400 mM. In another related embodiment the concentration of the excipient is from about 200 mM to about 300 mM. In still another related embodiment the concentration of the excipient is from about 140 mM to about 170 mM. Also provided are such pharmaceutical compositions having a pH between about 4.0 to about 8.0. In a related embodiment the pH is about 4.0 to about 6.0. In a further related embodiment the pH is about 4.8 to about 5.4.

Also provided is a method of preparing a lyophilized powder comprising the step of lyophilizing a pharmaceutical formulation as described above.

Provided herein is a lyophilized powder comprising a therapeutic protein and an excipient selected from the group consisting of n-acetyl arginine, n-acetyl lysine, n-acetyl histidine, n-acetyl proline and mixtures thereof wherein the excipient is present at a weight:weight concentration effective to reduce viscosity upon reconstitution with a diluent. In one embodiment the excipient is present at a concentration of between about 100 µg per mg therapeutic protein to about 1 mg per mg therapeutic protein. In a related embodiment the excipient is present at a concentration between about 200 µg to about 500 µg per mg therapeutic protein. In a further related embodiment the excipient is present at a concentration between about 150 µg to about 250 µg per mg therapeutic protein. Also provided is a method for reconstituting a lyophilized powder as described above comprising the step of adding a sterile aqueous diluent.

Also provided are therapeutic proteins that are antibodies. Also provided are formulations or compositions as described above wherein the therapeutic protein is an antibody. In addition, also provided herein is a lyophilized powder as described above wherein the therapeutic protein is an antibody.

DETAILED DESCRIPTION

Reducing the viscosity of high concentration therapeutic protein formulations is of interest to the pharmaceutical industry. The excipients, n-acetyl arginine, n-acetyl lysine, n-acetyl histidine, n-acetyl proline and mixtures thereof, were discovered to reduce the viscosity of such formulations. The invention provides the excipient at selected concentrations for use in reducing the viscosity of protein formulations. Methods for reducing the viscosity of protein formulations by combining the therapeutic protein with a viscosity-reducing concentration of an excipient selected from the group consisting of n-acetyl arginine, n-acetyl lysine, n-acetyl histidine, n-acetyl proline and mixtures thereof is provided herein. Also provided is lyophilized powder comprising a therapeutic protein and an excipient selected from the group consisting of n-acetyl arginine, n-acetyl lysine, n-acetyl histidine, n-acetyl proline and mixtures thereof, wherein the excipient is present at a weight:weight concentration effective to reduce viscosity upon reconstitution with a diluent.

Unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

All patents and other publications identified are expressly incorporated herein by reference in their entirety for the purpose of describing and disclosing, for example, the methodologies described in such publications that might be used in connection with the described.

Zwitterions are characterized as having separate positive and negative charges that result in a net zero charge for the compound. Most amino acids are zwitterions at physiological pH. As disclosed herein, pharmaceutical formulations containing zwitterions, in particular, n-acetyl arginine, n-acetyl lysine, n-acetyl histidine, n-acetyl proline and mixtures thereof, were found to generally have lower viscosity than polyol containing formulations while having greater or comparable stability.

N-acetyl arginine, n-acetyl lysine, n-acetyl histidine, and n-acetyl proline are modified versions of a naturally-occurring amino acids. N-acetyl arginine, n-acetyl lysine, n-acetyl histidine, and n-acetyl proline include both d and l forms of the amino acids, such as n-acetyl-1 arginine, n-acetyl-d arginine, n-acetyl-1 lysine, n-acetyl-d lysine, n-acetyl-1 histidine, n-acetyl-d histidine, n-acetyl-1 proline and n-acetyl-d proline.

The terms "polypeptide" and "protein" are used interchangeably herein. Exemplary polypeptides contemplated for use in the stable pharmaceutical formulations of the invention include antibodies, peptibodies, immunoglobulin-like proteins, non-antibody proteins and non-immunoglobulin-like proteins. Analogs of naturally occurring proteins are contemplated for inclusion in formulations of the present invention, including polypeptides with modified glycosylation, polypeptides without glycosylation (unglycosylated). As used herein, "analogs" refers to an amino acid sequence that has insertions, deletions or substitutions relative to the parent sequence, while still substantially maintaining the biological activity of the parent sequence, as determined using biological assays known to one of skill in the art. The formulations of the invention may also include derivatives of naturally occurring or analog polypeptides which have been chemically modified, for example, to attach water soluble polymers (e.g., pegylated), radionuclides, or other diagnostic or targeting or therapeutic moieties.

Antibodies may be formulated according to the present invention. As used herein, the term "antibody" includes fully assembled antibodies, monoclonal antibodies (including human, humanized or chimeric antibodies), polyclonal antibodies, multispecific antibodies (e.g., bispecific antibodies), maxibody, BiTes, DARTs, and antibody fragments that can bind antigen (e.g., Fab', F'(ab)2, Fv, single chain antibodies, diabodies), comprising complementarity determining regions (CDRs) of the foregoing as long as they exhibit the desired biological activity.

Peptibodies, molecules comprising an antibody Fc domain attached to at least one antigen-binding peptide, are generally described in PCT publication WO 00/24782 Immunoglobulin-like proteins, members of the immunoglobulin superfamily, contain one or more immunoglobulin-like domains which fold in structures similar to portions of the antibody variable region.

Proteins, including those that bind to one or more of the following, would be useful in the compositions and methods of the present invention. These include CD proteins including, but not limited to, CD3, CD4, CD8, CD19, CD20, CD22, CD30, and CD34; including those that interfere with receptor binding. HER receptor family proteins, including HER2, HER3, HER4, and the EGF receptor. Cell adhesion molecules, for example, LFA-I, MoI, p150, 95, VLA-4, ICAM-I, VCAM, and alpha v/beta 3 integrin. Growth factors, including but not limited to, vascular endothelial growth factor ("VEGF"), growth hormone, thyroid stimulating hormone, follicle stimulating hormone, luteinizing hormone, growth hormone releasing factor, parathyroid hormone, mullerian-inhibiting substance, human macrophage inflammatory protein (MIP-I-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors. Insulins and insulin-related proteins, including but not limited to insulin, insulin A-chain, insulin B-chain, proinsulin, and insulin-like growth factor binding proteins. Coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin; (vii) other blood and serum proteins, including but not limited to albumin, IgE, and blood group antigens. Colony stimulating factors and receptors thereof, including the following, among others, M-CSF, GM-CSF, and G-CSF, and receptors thereof, such as CSF-1 receptor (c-fms). Receptors and receptor-associated proteins, including, for example, flk2/flt3 receptor, obesity (OB) receptor, LDL receptor, growth hormone receptors, thrombopoietin receptors ("TPO-R," "c-mp1"), glucagon receptors, interleukin receptors, interferon receptors, T-cell receptors, stem cell factor receptors, such as c-Kit, and other receptors listed herein. Receptor ligands, including, for example, OX40L, the ligand for the OX40 receptor. Neurotrophic factors, including but not limited to, bone-derived neurotrophic factor (BDNF) and neurotrophin-3, -4, -5, or -6 (NT-3, NT-4, NT-5, or NT-6). Relaxin A-chain, relaxin B-chain, and prorelaxin; interferons and interferon receptors, including for example, interferon-$\alpha$, -$\beta$, and -$\gamma$, and their receptors. Interleukins and interleukin receptors, including but not limited to IL-I to IL-33 and IL-I to IL-33 receptors, such as the IL-8 receptor, among others. Viral antigens, including but not limited to, an AIDS envelope viral antigen. Lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAse, inhibin, and activin. Integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies. Myostatins, TALL proteins, including TALL-I, amyloid proteins, including but not limited to amyloid-beta proteins, thymic stromal lymphopoietins ("TSLP"), RANK ligand ("OPGL"), c-kit, TNF receptors, including TNF Receptor Type 1, TRAIL-R2, angiopoietins, and biologically active fragments or analogs or variants of any of the foregoing.

Exemplary proteins and antibodies include Activase® (Alteplase); alirocumab (anti-PCSK9 monoclonal antibody designated as H1H316P, see U.S. Pat. No. 8,062,640); Aranesp® (Darbepoetin-alfa), Epogen® (Epoetin alfa, or erythropoietin); Avonex® (Interferon β-Ia); Bexxar® (Tositumomab); Betaseron® (Interferon-β); bococizumab (anti-PCSK9 monoclonal antibody designated as L1L3, see U.S. Pat. No. 8,080,243); Campath® (Alemtuzumab); Dynepo® (Epoetin delta); Velcade® (bortezomib); MLN0002 (anti-α4β7 mAb); MLN1202 (anti-CCR2 chemokine receptor mAb); Enbrel® (etanercept); Eprex® (Epoetin alfa); Erbitux® (Cetuximab); evolocumab (anti-PCSK9 monoclonal antibody designated as 21B12, see U.S. Pat. No. 8,030,467); Genotropin® (Somatropin); Herceptin® (Trastuzumab); Humatrope® (somatropin [rDNA origin] for injection); Humira® (Adalimumab); Infergen® (Interferon Alfacon-1); Natrecor® (nesiritide); Kineret® (Anakinra), Leukine® (Sargamostim); LymphoCide® (Epratuzumab); Benlysta™ (Belimumab); Metalyse® (Tenecteplase); Mircera® (methoxy polyethylene glycol-epoetin beta); MyIotarg® (Gemtuzumab ozogamicin); Raptiva® (efalizumab); Cimzia® (certolizumab pegol); Soliris™ (Eculizumab); Pexelizumab (Anti-C5 Complement); MEDI-524 (Numax®); Lucentis® (Ranibizumab); Edrecolomab (Panorex®); Trabio® (lerdelimumab); TheraCim hR3 (Nimotuzumab); Omnitarg (Pertuzumab, 2C4); Osidem® (IDM-I); OvaRex® (B43.13); Nuvion® (visilizumab); Cantuzumab mertansine (huC242-DM1); NeoRecormon® (Epoetin beta); Neumega® (Oprelvekin); Neulasta® (Pegylated filgastrim, pegylated G-CSF, pegylated hu-Met-G-CSF); Neupogen® (Filgrastim); Orthoclone OKT3® (Muromonab-CD3), Procrit® (Epoetin alfa); Remicade® (Infliximab), Reopro® (Abciximab), Actemra® (anti-IL6 Receptor mAb), Avastin® (Bevacizumab), HuMax-CD4 (zanolimumab), Rituxan® (Rituximab); Tarceva® (Erlotinib); Roferon-A®-(Interferon alfa-2a); Simulect® (Basiliximab); Stelara™ (Ustekinumab); Prexige® (lumiracoxib); Synagis® (Palivizumab); 146B7-CHO (anti-IL15 antibody, see U.S. Pat. No. 7,153,507), Tysabri® (Natalizumab); Valortim® (MDX-1303, anti-*B. anthracis* Protective Antigen mAb); ABthrax™; Vectibix® (Panitumumab); Xolair® (Omalizumab), ETI211 (anti-MRSA mAb), IL-I Trap (the Fc portion of human IgG1 and the extracellular domains of both IL-I receptor components (the Type I receptor and receptor accessory protein)), VEGF Trap (Ig domains of VEGFR1 fused to IgG1 Fc), Zenapax® (Daclizumab); Zenapax® (Daclizumab), Zevalin® (Ibritumomab tiuxetan), Zetia (ezetimibe), Atacicept (TACI-Ig), anti-α4β7 mAb (vedolizumab); galiximab (anti-CD80 monoclonal antibody), anti-CD23 mAb (lumiliximab); BR2-Fc (huBR3/huFc fusion protein, soluble BAFF antagonist); Simponi™ (Golimumab); Mapatumumab (human anti-TRAIL Receptor-1 mAb); Ocrelizumab (anti-CD20 human mAb); HuMax-EGFR (zalutumumab); M200 (Volociximab, anti-α5β1 integrin mAb); MDX-010 (Ipilimumab, anti-CTLA-4 mAb and VEGFR-I (IMC-18F1); anti-BR3 mAb; anti-*C. difficile* Toxin A and Toxin B C mAbs MDX-066 (CDA-I) and MDX-1388); anti-CD22 dsFv-PE38 conjugates (CAT-3888 and CAT-8015); anti-CD25 mAb (HuMax-TAC); anti-TSLP antibodies (see U.S. Pat. Nos. 7,982,016, 8,232,372 and U.S. Publication Application 20090186022); anti-TSLP receptor antibody (see U.S. Pat. No. 8,101,182); anti-TSLP antibody designated as A5 (see U.S. Pat. No. 7,982,016); (see anti-CD3 mAb (NI-0401); Adecatumumab (MT201, anti-EpCAM-CD326 mAb); MDX-060, SGN-30, SGN-35 (anti-CD30 mAbs); MDX-1333 (anti-IFNAR); HuMax CD38 (anti-CD38 mAb); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-sclerostin antibodies (see, U.S. Pat. Nos. 8,715,663 or 7,592,429). Anti-sclerostin antibody designated as Ab-5 (see U.S. Pat. Nos. 8,715,663 or 7,592,429); anti-ganglioside GM2 mAb; anti-GDF-8 human mAb (MYO-029); anti-GM-CSF Receptor mAb (CAM-3001); anti-HepC mAb (HuMax HepC); MEDI-545, MDX-1103 (anti-IFNα mAb); anti-IGFIR mAb; anti-IGF-IR mAb (HuMax-Inflam); anti-IL12/IL23p40 mAb (Briakinumab); anti-IL-23p19 mAb (LY2525623); anti-IL13 mAb (CAT-354); anti-IL-17 mAb (AIN457); anti-IL2Ra mAb (HuMax-TAC); anti-IL5 Receptor mAb; anti-integrin receptors mAb (MDX-018, CNTO 95); anti-IPIO Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1 106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; NVS Antibody #2; and an amyloid-beta monoclonal antibody comprising sequences, SEQ ID NO:8 and SEQ ID NO:6 (see U.S. Pat. No. 7,906,625).

Exemplary protein concentrations in the formulation may range from about 70 mg/ml to about 300 mg/ml, about 120 mg/ml to about 270 mg/ml, from about 140 mg/ml to about 255 mg/ml, from about 140 mg/ml to about 240 mg/ml, or from about 140 mg/ml to about 220 mg/ml, or alternatively from about 190 mg/ml to about 210 mg/ml. The concentration of protein will depend upon the end use of the pharmaceutical formulation and can be easily determined by a person of skill in the art. Particularly contemplated concentrations of protein are at least about 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 and 300 mg/ml and including all values in between.

As used herein, "pharmaceutical formulation" is a sterile composition of a pharmaceutically active drug, such as a biologically active protein, that is suitable for parenteral administration (including but not limited to intravenous, intramuscular, subcutaneous, aerosolized, intrapulmonary, intranasal or intrathecal) to a patient in need thereof and includes only pharmaceutically acceptable excipients, diluents, and other additives deemed safe by the Federal Drug Administration or other foreign national authorities. Pharmaceutical formulations include liquid, e.g. aqueous, solutions that may be directly administered, and lyophilized powders which may be reconstituted into solutions by adding a diluent before administration. Specifically excluded from the scope of the term "pharmaceutical formulation" are compositions for topical administration to patients, compositions for oral ingestion, and compositions for parenteral feeding.

"Shelf life", as used herein, means that the storage period during which an active ingredient such as a therapeutic protein in a pharmaceutical formulation has minimal degradation (e.g., not more than about 5% to 10% degradation) when the pharmaceutical formulation is stored under specified storage conditions, for example, 2-8° C. Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. The pharmaceutical formulations of the present invention preferably exhibit not more than about 5 to 10% increases in degradation (e.g., fragmentation, aggregation or unfolding) over two years when stored at 2-8° C.

As used herein, "stable" formulations of biologically active proteins are formulations that exhibit reduced aggregation and/or reduced loss of biological activity of at least 20% upon storage at 2-8° C. for at least 2 years compared with a control formula sample, or alternatively which exhibit reduced aggregation and/or reduced loss of biological activity under conditions of thermal stress, e.g. 25° C. for 1 week to 12 weeks; 40° C. for 1 to 12 weeks; 52° C. for 7-8 days, etc.

As used herein, "viscosity" is a fluid's resistance to flow, and may be measured in units of centipoise (cP) or milli-Pascal-second (mPa-s), where 1 cP=1 mPa-s, at a given shear rate. Viscosity may be measured by using a viscometer, e.g., Brookfield Engineering Dial Reading Viscometer, model LVT, and AR-G2, TA instruments. Viscosity may be measured using any other methods and in any other units known in the art (e.g. absolute, kinematic or dynamic viscosity), understanding that it is the percent reduction in viscosity afforded by use of the excipients described by the invention that is important. Regardless of the method used to determine viscosity, the percent reduction in viscosity in excipient formulations versus control formulations will remain approximately the same at a given shear rate.

As used herein, a formulation containing an amount of an excipient effective to "reduce viscosity" (or a "viscosity-reducing" amount or concentration of such excipient) means that the viscosity of the formulation in its final form for administration (if a solution, or if a powder, upon reconstitution with the intended amount of diluent) is at least 5% less than the viscosity of an appropriate control formulation, such as water, buffer, other known viscosity-reducing agents such as salt, etc. and those control formulations, for example, exemplified herein. Excipient-free control formulations might also be used even if they may not be implementable as a therapeutic formulation due to hypotonicity, for instance.

Similarly, a "reduced viscosity" formulation is a formulation that exhibits reduced viscosity compared to a control formulation.

Protein therapeutics often need to be given at high concentrations which can result in increased viscosity of the solution. It is highly desirable to provide high concentration formulations that do not exhibit the increased viscosity typically seen with such high protein concentrations.

High viscosity formulations are difficult to handle during manufacturing, including at the bulk and filling stages. High viscosity formulations are also difficult to draw into a syringe and inject, often necessitating use of lower gauge needles which can be unpleasant for the patient. The addition of n-acetyl-1-arginine to solutions of biologically active protein reduced the viscosity of high concentration protein solutions.

The use of an excipient selected from the group consisting of n-acetyl arginine, n-acetyl lysine, n-acetyl histidine, n-acetyl proline and mixtures thereof permits a higher concentration of therapeutic proteins to be used in the formulation without as great of an increase in viscosity as is typically seen with other excipients. Thus, the invention provides a method for stabilizing or reducing viscosity of protein formulations by adding an excipient selected from the group consisting of n-acetyl arginine, n-acetyl lysine, n-acetyl histidine, n-acetyl proline and mixtures thereof in an amount effective to reduce viscosity. The invention also provides reduced viscosity formulations of therapeutic proteins, including antibodies, containing effective amounts or concentrations of an excipient selected from the group consisting of n-acetyl arginine, n-acetyl lysine, n-acetyl histidine, n-acetyl proline and mixtures thereof. Also contemplated are methods of screening one or more formulations, each containing different concentrations of the excipient described herein to identify suitable or optimal concentrations that reduce viscosity. Further provided are methods of preparing a lyophilized powder from reduced viscosity solution formulations of the invention, and methods of reconstituting the lyophilized powders of the invention via addition of a sterile diluent.

Thus, the present invention provides pharmaceutical formulations containing biologically active polypeptides and viscosity-reducing concentrations of an excipient selected from the group consisting of n-acetyl arginine, n-acetyl lysine, n-acetyl histidine, n-acetyl proline and mixtures thereof. The reduction in viscosity is at least about 5-90% versus control formulations. In one embodiment the reduction in viscosity ranges from about 10-80%. In other exemplary embodiments, the reduction in viscosity is at least 5%, 10%, 15%, 20%, 25%, 30%, 35%, 40%, 45%, 50%, 55%, 60%, 65%, 70%, 75%, 80% or 85%.

Formulations of the invention may optionally include pharmaceutically acceptable salts, buffers, surfactants, other excipients, carriers, diluents, and/or other formulation agents.

Exemplary pharmaceutically acceptable buffers include acetate (e.g. sodium acetate), succinate (such as sodium succinate), glutamic acid, glutamate, gluconate, histidine, citrate or other organic acid buffers. Exemplary buffer concentration can be from about 1 mM to about 200 mM, or from about 10 mM to about 60 mM, depending, for example, on the buffer and the desired tonicity (e.g. isotonic, hypertonic or hypotonic) of the formulation. Exemplary pHs include from about 4.5 to about 8.0, or from about 4.8 to about 5.5, or from about 4 to 6, or about 5 to 5.5, or about 5, greater than about 5, greater than about 5.5, greater than about 6, or greater than about 6.5.

Suitable diluents, other excipients, or carriers and other agents include, but are not limited to, antioxidants, coloring, flavoring and diluting agents, emulsifying agents, suspending agents, solvents, fillers, bulking agents, buffers, vehicles, diluents and/or pharmaceutical adjuvants. For example, a suitable vehicle may be, physiological saline solution, citrate buffered saline, or artificial CSF, possibly supplemented with other materials common in compositions for parenteral administration. Neutral buffered saline or saline mixed with serum albumin are further exemplary vehicles. Those skilled in the art would readily recognize a variety of buffers that could be used in the compositions, and dosage forms used in the invention. Typical buffers include, but are not limited to pharmaceutically acceptable weak acids, weak bases, or mixtures thereof. Exemplary buffer components are water soluble materials such as phosphoric acid, tartaric acids, lactic acid, succinic acid, citric acid, acetic acid, ascorbic acid, aspartic acid, glutamic acid, or salts thereof. Exemplary salts include inorganic and organic acids, or bases such as metals or amines, in exemplary concentrations such as about 50-200 mM, or 100-200 mM, or about 100 mM, or about 150 mM.

Other excipients or stabilizers may also be included, for example, sugars (e.g., sucrose, glucose, trehalose, fructose, xylose, mannitose, fucose), polyols (e.g., glycerol, mannitol, sorbitol, glycol, inositol), amino acids or amino acid derivatives (e.g., arginine, proline, histidine, lysine, glycine, methionine, etc.) or surfactants (e.g., polysorbate, including polysorbate 20, or polysorbate 80, or poloxamer, including poloxamer 188, TPGS (d-alpha tocopheryl polyethylene glycol 1000 succinate). Exemplary concentrations of surfactant may range from about 0.001% to about 1.0%, or from about 0.003% to about 0.5%. Preservatives may also be included, such as benzyl alcohol, phenol, m-cresol, chlorobutanol or benzethonium Cl, e.g. at concentrations ranging from about 0.1% to about 2%, or from about 0.5% to about 1%.

One or more other pharmaceutically acceptable carriers, excipients or stabilizers such as those described in Remington's Pharmaceutical Sciences 21st edition, Osol, A. Ed. (2005) may be included in the formulation provided that they do not adversely affect the desired characteristics of the formulation.

The concentration of the therapeutic protein, such as an antibody, in the formulation will depend upon the end use of the pharmaceutical formulation and can be easily determined by a person of skill in the art.

Therapeutic proteins that are antagonists are frequently administered at higher concentrations than those that are agonists. Particularly contemplated high concentrations of therapeutic proteins (without taking into account the weight of chemical modifications such as pegylation), including antibodies, are at least about 70, 80, 90, 100, 110, 120, 130, 140, 150, 175, 180, 185, 190, 195 200, 250, 300, 350, 400, 450, or 500 mg/ml, and/or less than about 250 300, 350, 400, 450 or 500 mg/ml. Exemplary high concentrations of therapeutic proteins, such as antibodies, in the formulation may range from at least about 100 mg/ml to about 500 mg/ml. Other protein concentrations (without taking into account the weight of chemical modifications such as pegylation), are also contemplated, e.g., at least about 1, 5, 10, 20, 30, 35, 40, 45, 50, 55, 60, 65 or 70 mg/ml. The invention particularly contemplates formulations and methods in which the concentration of therapeutic protein results in a viscosity of at least 6, 8, 10, 12, 14, 16, 18, 20, 25, 30, 35 cP or higher, such as 100, 125, 150, 175 or 200 cP and the inclusion of an excipient selected from the group consisting of n-acetyl arginine, n-acetyl lysine, n-acetyl histidine, n-acetyl proline and mixtures thereof results in the reduction of the viscosity by 5% or greater. For example, a solution with a viscosity of about 30 cP may be difficult to inject with a standard 27 gauge needle. All references to mg/ml concentration of therapeutic protein, weight of therapeutic protein (mg) or molecular weight of therapeutic protein (kD) herein mean the respective weight of the proteinaceous part of the therapeutic protein, excluding any non-proteinaceous modifications.

The present invention provides a method of reducing the viscosity of and/or improving stability of a liquid pharmaceutical formulation of a therapeutic protein, by combining the therapeutic protein and a viscosity-reducing amount of an excipient selected from the group consisting of n-acetyl arginine, n-acetyl lysine, n-acetyl histidine, n-acetyl proline and mixtures thereof.

In exemplary embodiments, the therapeutic protein is at a high protein concentration as described above. In some embodiments, the reduction in viscosity is at least about 5%, 10%, 15%, 20%, 25%, 30%, 35%, 40%, 45%, 50%, 55%, 60%, 65%, 70%, 75%, 80% or 85% compared to control formulations In another aspect, the invention provides liquid solutions comprising a therapeutic protein and an excipient selected from the group consisting of n-acetyl arginine, n-acetyl lysine, n-acetyl histidine, n-acetyl proline and mixtures thereof wherein the formulations exhibit reduced viscosity relative to control formulations. In exemplary embodiments, the therapeutic protein is at a high protein concentration as described above. In some embodiments, the excipient described herein is present at a viscosity-reducing (weight: volume) concentration. Any of these excipients can be used at concentrations up to their solubility limit. Such solutions may further comprise a sugar or other polyol such as sucrose or sorbitol, or an amino acid such as arginine, proline, histidine, lysine, glycine, methionine, etc. in an amount effective to further improve stability, reduce aggregation, and/or make the formulation isotonic, without significantly increasing viscosity.

In exemplary embodiments, the concentration of the excipient selected from the group consisting of n-acetyl arginine, n-acetyl lysine, n-acetyl histidine, n-acetyl proline and mixtures thereof is at least about 50 mM to about 300 mM, or at least about 100 mM to about 250 mM, or at least about 140 mM to about 200 mM. In exemplary embodiments the concentration of the excipient is at least about 50, 100, 105, 110, 115, 120, 125, 130, 135, 140, 145, 150, 155, 160, 165, 170, 175, 180, 185, 190, 195, 200, 210, 220, 250, or 300 mM or greater. Other exemplary embodiments include concentrations of excipients effective to make the formulation isotonic, without significantly increasing viscosity. Exemplary concentrations include those at least about 180 mM or greater, in further embodiments the amounts are at least about 200 mM or greater.

In another aspect, the invention provides lyophilized protein formulations comprising a therapeutic protein and an excipient selected from the group consisting of n-acetyl arginine, n-acetyl lysine, n-acetyl histidine, n-acetyl proline and mixtures thereof wherein upon reconstitution with the recommended amount of diluent, the formulations exhibit reduced viscosity relative to control formulations. In exemplary embodiments, the therapeutic protein is at a high protein concentration as described above. In some embodiments, the excipient is present at an amount effective to reduce viscosity upon reconstitution with diluent (weight:weight concentration). Such formulations may further comprise a sugar or other polyol such as sucrose or sorbitol, or at least one amino acid such as arginine, proline, histidine, lysine, glycine, methionine, etc., in an amount effective to further improve stability, reduce aggregation, and/or make the formulation isotonic, without significantly increasing viscosity.

In exemplary embodiments, the concentration of the excipient selected from the group consisting of n-acetyl arginine, n-acetyl lysine, n-acetyl histidine, n-acetyl proline and mixtures thereof is at least about 1 µg per mg therapeutic protein, up to about 1.0 mg per mg therapeutic protein. In some embodiments, the concentration of excipient is at least about 1, 10, 50, 100, 150, 200, 250, 300, 350, 400, 450, 500 or 550 µg per mg therapeutic protein. In other exemplary embodiments, the concentration of excipient is up to about 600, 650, 700, 750, 800, 850, 900, 950 or 1000 µg per mg therapeutic protein.

In yet another embodiment, the present invention provides a method of preventing self-association of proteins in liquid formulations by using n-acetyl arginine, n-acetyl lysine, n-acetyl histidine, n-acetyl proline and mixtures thereof as an excipient in any of the amounts or concentrations described herein. Formulations with improved stability (e.g., reduced aggregation) and shelf-life are also provided.

The invention also provides a kit comprising a liquid protein formulation of the invention, and instructions for its administration, optionally with a container, syringe and/or other administration device. The invention further provides a kit comprising a lyophilized protein formulation of the invention, optionally in a container, and instructions for its reconstitution and administration, optionally with a vial of sterile diluent, and optionally with a syringe or other administration device. Exemplary containers include vials, tubes, bottles, single or multi-chambered pre-filled syringes, or cartridges. Exemplary administration devices include syringes, with or without needles, infusion pumps, jet injectors, pen devices, transdermal injectors, or other needle-free injector, or an aerosolization device for nasal or pulmonary delivery.

In another aspect, a method is provided for screening for a viscosity-reducing concentration of an excipient comprising the steps of: (1) assessing the viscosity of a first solution comprising a first concentration of an excipient selected from the group consisting of n-acetyl arginine, n-acetyl lysine, n-acetyl histidine, n-acetyl proline and mixtures thereof and a therapeutic protein, such as an antibody, (2) assessing the viscosity of a second solution comprising a different second concentration of the excipient and the therapeutic protein, and (3) determining that the first concentration of excipient is more viscosity-reducing than the second concentration of excipient if the first solution is less viscous. Viscosity can be determined, e.g., using an Aries ARG2 Rheometer or a Brookfield RV-DVIII Rheometer.

Similar methods are provided for screening for an aggregation-reducing or stabilizing concentration of an excipient.

Stability can be assessed in many ways, including monitoring conformational change over a range of temperatures (thermostability) and/or time periods (shelf-life) and/or after exposure to stressful handling situations (e.g. physical shaking). Stability of formulations containing varying concentrations of formulation components can be measured using a variety of methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein. Fluorescence can also be used to analyze the composition. Fluorescence encompasses the release or absorption of energy in the form of light or heat, and changes in the polar properties of light. Fluorescence emission can be intrinsic to a protein or can be due to a fluorescence reporter molecule. For example, ANS is a fluorescent probe that binds to the hydrophobic pockets of partially unfolded proteins. As the concentration of unfolded protein increases, the number of hydrophobic pockets increases and subsequently the concentration of ANS that can bind increases. This increase in ANS binding can be monitored by detection of the fluorescence signal of a protein sample. Other means for measuring stability can be used and are well known to persons of skill in the art.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Example 1

An IgG2 antibody preparation (140 mg/ml)(Antibody A) was dialyzed against 10 mM Sodium Glutamate 1% Sucrose pH 5.2 using Snakeskin® pleated dialysis tubing 10,000 MWCO (Thermo Fisher Scientific, Waltham, Mass.). 120 mg/mL Antibody A in 10 mM Sodium Glutamate 1% Sucrose pH 5.2 was filled in 3 cc vials at 1 mL fill each. Vials were lyophilized using a Virtis lyophilizer. Vials were reconstituted with 450 uL of various solutions (water—control or 200 mM excipient solutions). Following reconstitution, Antibody A concentrations were determined using SOLO- VPE instrument to be 190 mg/mL. Viscosity was measured using Aries ARG2 rheometer at 25° C. and are recorded in Table 1 below.

TABLE 1

Excipient formulations of Antibody A, 190 mg/mL at 20° C.

| Buffer Identification | Excipient |
|---|---|
| A | 200 mM Proline |
| B | 200 mM Arginine Glutamate |
| C | 200 mM n-Acetyl-l Arginine |
| D | 200 mM Guanidinopropionate |
| E | 200 mM Taurocyamine |
| F | 200 mM n-acetyl-l Proline |
| G | 200 mM n-acetyl-l Glycine |
| H | 200 mM n-acetyl-l Lysine |
| I | water control |

Figure 1:
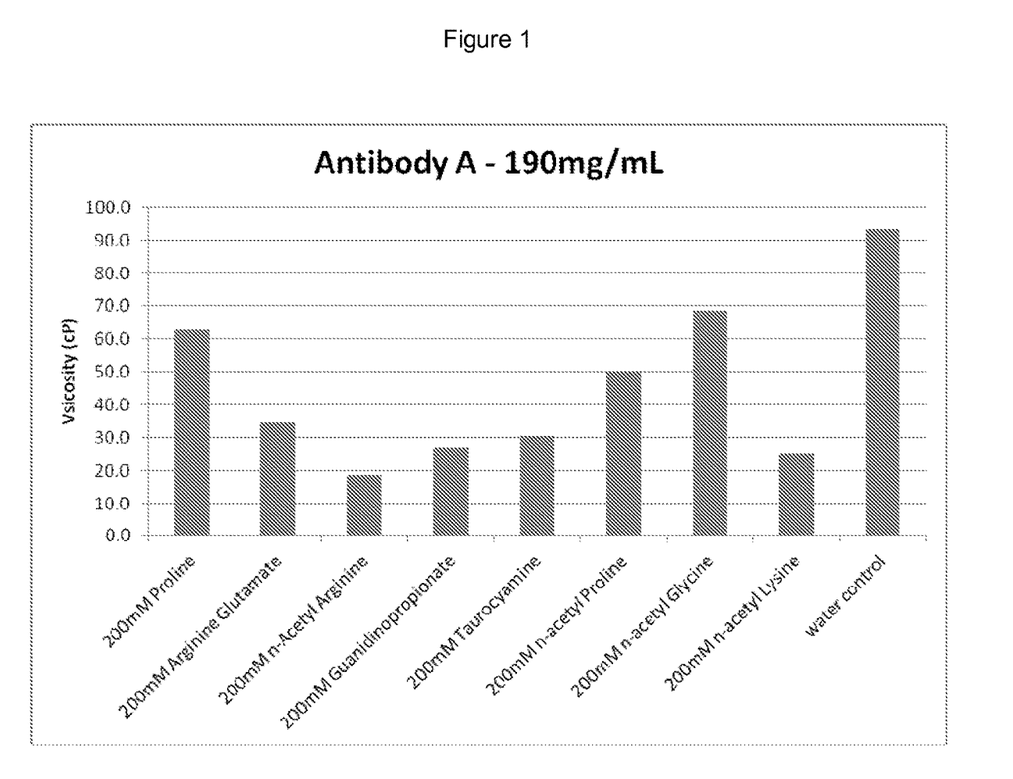
FIG. 1 is a bar graph showing the effects of various excipients on the viscosity of an antibody solution.

FIG. 1 shows the effects of the various excipients on the viscosity of the antibody solution. The data shows that the tested excipients have reduced viscosity relative to the water control.

Example 2

An IgG1 antibody preparation (70 mg/ml)(Antibody B) and an IgG2 antibody preparation (70 mg/ml)(Antibody C) were dialyzed against 20 mM Sodium Acetate pH 4.7 and 4.9 respectively using 10,000 MWCO dialysis tubing. Antibody samples were concentrated using 30,000 MWCO centrifugal filters and an Allegra X-12R Centrifuge. Antibody sample concentrations were determined using an Agilent UV/Vis Spectrophotometer. Excipient-containing samples were prepared by spiking a bulk concentrated solution with pre-weighed solid excipients. Viscous samples were transferred using positive displacement pipettes. Viscosities were measured using a Brookfield RV-DV III+ Programmable Rheometer at 25° C. and are recorded in Tables 2.1 and 2.2 below.

TABLE 2.1

Antibody B-210 mg/mL

| Formulation | Viscosity (cP), 225/s, 25° C. |
|---|---|
| Control No Excipient | 26.0 |
| 200 mM n-Acetyl-L Arginine | 14.3 |

TABLE 2.2

Antibody C-140 mg/mL

| Formulation | Viscosity (cP) 225/s, 25° C. |
|---|---|
| Control No Excipient | 22.7 |
| 200 mM n-Acetyl-L Arginine | 10.0 |

For the excipient, n-acetyl-1 arginine, the decrease in viscosity of Antibody B is approximately 45%, and the decrease in viscosity of Antibody C is approximately 56%.

Example 3

An IgG2 antibody preparation (140 mg/ml)(Antibody D) was dialyzed against 10 mM Sodium Glutamate 1% Sucrose pH 5.2 using Snakeskin® pleated dialysis tubing 10,000 MWCO (Thermo Fisher Scientific, Waltham, Mass.). 100 mg/mL Antibody D in 10 mM Sodium Glutamate 1% Sucrose pH 5.2 was filled in 3 cc vials at 1 mL fill each. Vials were lyophilized using Virtis lyophilizer. Vials were reconstituted with 450 uL of either water (control No excipient) or 10 mM Glutamate 200 mM n-Acetyl-L Arginine pH 5.2. Antibody D concentrations were determined using SOLO-VPE instrument. Viscosity was measured using Aries ARG2 rheometer at 25° C. and are recorded in Table 3.0 below.

TABLE 3.0

Antibody D-175 mg/mL

| Formulation | Viscosity (cP) 1000/s, 25° C. |
|---|---|
| Control No Excipient | 38.7 |
| 200 mM n-Acetyl-l Arginine | 23.4 |

For the excipient, n-acetyl-1 arginine, the decrease in viscosity of Antibody D is approximately 40%.

Example 4

An IgG2 antibody preparation (140 mg/ml)(Antibody E) was concentrated using ultrafiltration and diafiltration to 200 mg/ml with 6 diafiltration volumes of Buffer A (10 mM Glutamate 260 mM n-acetyl-1 arginine pH 4.6) or Buffer B (10 mM Sodium Glutamate pH 4.6). Final pH of UFDF samples was determined to be 5.2. Antibody E concentrations were determined using SOLO-VPE instrument. Viscosity was measured using Aries ARG2 rheometer at 20° C., and recorded in Table 4.0 below.

TABLE 4.0

Antibody E-200 mg/mL

| Formulation | Viscosity (cP) 1000/s, 20° C. |
|---|---|
| Antibody E in Buffer B (Control) | 62.1 |
| Antibody E in Buffer A (260 mM n-acetyl-L-arginine) | 28.6 |

For the excipient, n-acetyl-1 arginine, the decrease in viscosity of Antibody E is approximately 54%.

Example 5

An IgG2 antibody preparation (140 mg/ml)(Antibody A) was dialyzed against 10 mM Sodium Glutamate 1% Sucrose pH 5.2 using Snakeskin® pleated dialysis tubing 10,000 MWCO (Thermo Fisher Scientific, Waltham, Mass.). 120 mg/mL Antibody A in 10 mM Sodium Glutamate 1% Sucrose pH 5.2 was filled in 3 cc vials at 1 mL fill each. Vials were lyophilized using a Virtis lyophilizer. Vials were reconstituted with 450 uL of various solutions (water control or 200 mM excipient solutions) (see Table 5 below). Following reconstitution, Antibody A concentrations were determined using SOLO-VPE instrument to be 190 mg/mL. Viscosity was measured using Aries ARG2 rheometer at 25° C. and are recorded in Table 5 below.

TABLE 5

Excipient formulations of Antibody A, 190 mg/mL at 20° C.

| Buffer Identification | Excipient |
|---|---|
| A | 200 mM Histidine |
| B | 200 mM n-Acetyl-L-Histidine |
| C | 200 mM n-Acetyl-L Arginine |
| D | control |

Figure 2:
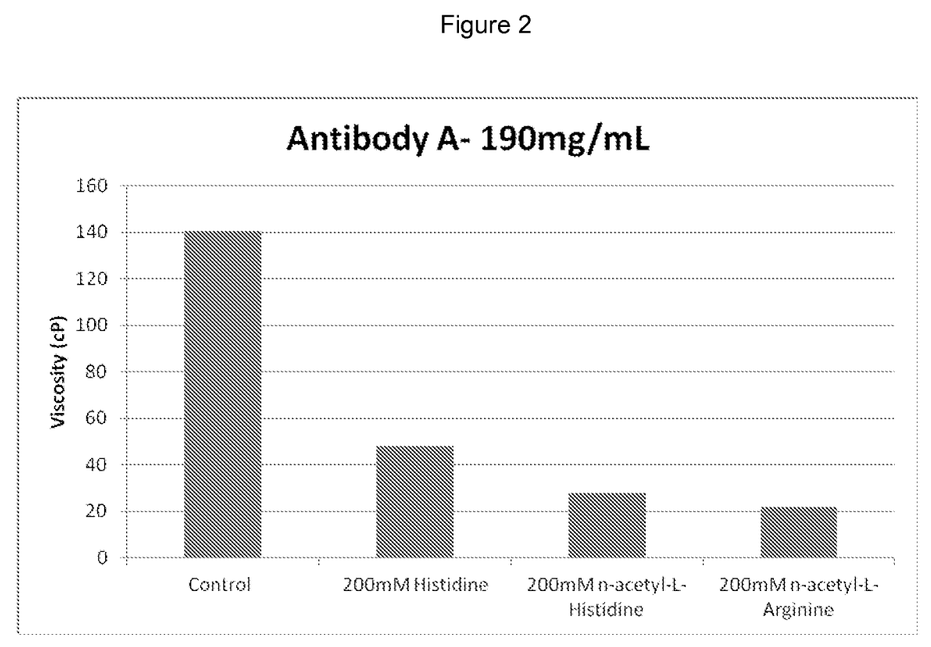
FIG. 2 is a bar graph showing the effects of various excipients on the viscosity of an antibody solution.

FIG. 2 shows the effects of the various excipients on the viscosity of the antibody solution. The data shows that the tested excipients have reduced viscosity relative to the control, and the excipients, n-acetyl-1 arginine and n-acetyl-1 histidine, have reduced viscosity relative to the excipient histidine alone.

What is claimed is:

1. A method for reducing the viscosity of a liquid pharmaceutical formulation comprising an antibody at a concentration of at least 70 mg/ml, comprising combining the antibody with a viscosity-reducing concentration of an excipient selected from the group consisting of the n-acetyl arginine, n-acetyl lysine, n-acetyl histidine, n-acetyl proline and mixtures thereof, wherein the viscosity of the liquid pharmaceutical formulation is reduced by at least 5% versus a control formulation.

2. The method of claim 1 wherein the excipient is n-acetyl arginine.

3. The method of claim 1 wherein the excipient is n-acetyl lysine.

4. The method of claim 1 wherein the excipient is n-acetyl histidine.

5. The method of claim 1 wherein the excipient is n-acetyl proline.

6. The method of claim 1 wherein viscosity of the formulation is reduced by at least 25%.

7. The method of claim 1 wherein viscosity of the formulation is reduced by at least 50%.

8. The method of claim 1 wherein viscosity of the formulation is reduced by at least 80%.

9. A pharmaceutical formulation produced by the method of claim 1.

10. The method of claim 1, comprising combining the excipient with the therapeutic protein at an excipient concentration of at least 50 mM.

11. The method of claim 1, comprising combining the excipient with the therapeutic protein at an excipient concentration of 50 mM to 300 mM.

12. The method of claim 1, comprising combining the excipient with the therapeutic protein at an excipient concentration of 100 mM to 400 mM.

13. The method of claim 1, comprising combining the excipient with the therapeutic protein at an excipient concentration of less than 200 mM.

14. The method of claim 2, wherein the concentration of the antibody is at least 140 mg/mL.

15. A pharmaceutical composition comprising an antibody at a concentration of at least 70 mg/ml and an excipient selected from the group consisting of n-acetyl arginine, n-acetyl lysine, n-acetyl histidine, n-acetyl proline and mixtures thereof at a viscosity-reducing concentration, wherein the viscosity is reduced by at least 5% versus a control formulation and the concentration of the excipient is less than about 200 mM.

16. The pharmaceutical composition of claim 15, wherein the excipient is n-acetyl arginine.

17. The pharmaceutical composition of claim 15, wherein the excipient is n-acetyl lysine.

18. The pharmaceutical composition of claim 15, wherein the excipient is n-acetyl histidine.

19. The pharmaceutical composition of claim 15, wherein the excipient is n-acetyl proline.

20. The pharmaceutical composition of claim 15 having a pH between about 4.0 to about 8.0.

21. The pharmaceutical composition of claim 20 having a pH of about 4.6 to about 5.4.

22. A method of preparing a lyophilized powder comprising the step of lyophilizing the pharmaceutical composition of claim 15.

23. The pharmaceutical composition of claim 16, wherein the concentration of the antibody is at least 140 mg/mL.

24. The method of any one of claim 1 or 22 wherein the antibody is an IgG2 monoclonal antibody.

25. The pharmaceutical formulation or pharmaceutical composition of claim 9 or 15 wherein the antibody is an IgG2 monoclonal antibody.

26. A method for reducing the viscosity of a liquid pharmaceutical formulation comprising a therapeutic protein at a concentration of at least 70 mg/ml, comprising combining the therapeutic protein with a viscosity-reducing concentration of an excipient selected from the group consisting of the n-acetyl lysine, n-acetyl histidine, n-acetyl proline and mixtures thereof, wherein the viscosity of the liquid pharmaceutical formulation is reduced by at least 5% versus a control formulation.

27. The method of claim 26, wherein the excipient is n-acetyl lysine.

28. The method of claim 26, wherein the excipient is n-acetyl histidine.

29. The method of claim 26, wherein the excipient is n-acetyl proline.

30. The method of claim 26, comprising combining the excipient with the therapeutic protein at an excipient concentration of at least 50 mM.

31. A pharmaceutical composition comprising a therapeutic protein at a concentration of at least 70 mg/ml and an excipient selected from the group consisting of n-acetyl lysine, n-acetyl histidine, n-acetyl proline and mixtures thereof at a viscosity-reducing concentration, wherein the viscosity is reduced by at least 5% versus a control formulation and the concentration of the excipient is less than about 200 mM.

32. The pharmaceutical composition of claim 31, wherein the excipient is n-acetyl lysine.

33. The pharmaceutical composition of claim 31, wherein the excipient is n-acetyl histidine.

34. The pharmaceutical composition of claim 31, wherein the excipient is n-acetyl proline.

35. The pharmaceutical composition of claim 31, having a pH of about 4.6 to about 5.4.

* * * * *

UNITED STATES PATENT AND TRADEMARK OFFICE
CERTIFICATE OF CORRECTION

| | | |
|---|---|---|
| PATENT NO. | : 11,813,328 B2 | Page 1 of 1 |
| APPLICATION NO. | : 15/521057 | |
| DATED | : November 14, 2023 | |
| INVENTOR(S) | : Sloey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 49 days.

Signed and Sealed this
Third Day of December, 2024

Katherine Kelly Vidal
*Director of the United States Patent and Trademark Office*